United States Patent
Buttgen et al.

(10) Patent No.: US 6,355,017 B2
(45) Date of Patent: Mar. 12, 2002

(54) CANNULA FOR MEDICAL SYRINGES

(75) Inventors: Heinz Buttgen; Tilo Callenbach, both of Jona (CH)

(73) Assignee: H. Weidmann A.G., Rapperswil (CH)

( * ) Notice: Subject to any disclaimer, the term of this patent is extended or adjusted under 35 U.S.C. 154(b) by 0 days.

(21) Appl. No.: 09/331,234

(22) PCT Filed: Oct. 1, 1997

(86) PCT No.: PCT/CH97/00367

§ 371 Date: Jun. 18, 1999

§ 102(e) Date: Jun. 18, 1999

(87) PCT Pub. No.: WO98/28031

PCT Pub. Date: Jul. 2, 1998

(30) Foreign Application Priority Data

Dec. 23, 1996 (CH) ............................................ 3175/96

(51) Int. Cl.[7] ................................................ A61M 5/00
(52) U.S. Cl. ...................................... 604/110; 604/195
(58) Field of Search .............................. 604/195, 192, 604/198, 240, 241, 243, 110, 263; 600/578

(56) References Cited

U.S. PATENT DOCUMENTS

| 3,662,457 A | 5/1972 | Gores |
| 5,114,404 A | 5/1992 | Paxton et al. |
| 5,480,385 A | 1/1996 | Thorne et al. |
| 5,531,705 A | * 7/1996 | Alter et al. ................. 604/195 |
| 5,685,863 A | * 11/1997 | Boitch et al. ............... 604/198 |
| 5,800,395 A | * 9/1998 | Botich et al. ........... 604/195 X |
| 6,015,396 A | * 1/2000 | Buttgen et al. ......... 604/110 X |

FOREIGN PATENT DOCUMENTS

| EP | 287 950 | 10/1988 |
| EP | 290 176 | 11/1988 |
| WO | WO 92/05818 | 4/1992 |
| WO | WO 92/16248 | 10/1992 |

* cited by examiner

*Primary Examiner*—Anhtuan T. Nguyen
(74) *Attorney, Agent, or Firm*—Sughrue Mion, PLLC

(57) ABSTRACT

A cannula is retractably mounted with a needle holder (9) in a housing (5). A switching device (7, 8) allows the hollow needle (10) to be retracted after use into the housing (5). The needle holder (9) secures against rotation the hollow needle (10) in the housing (5) in a predetermined orientation. The housing (5) is preferably provided on its outer side with markings (13) which indicate the orientation of the hollow needle (10). The hollow needle (9) cannot twist when it is retracted. Another advantage is that the orientation of the needle point need not be determined before making an injection.

20 Claims, 2 Drawing Sheets

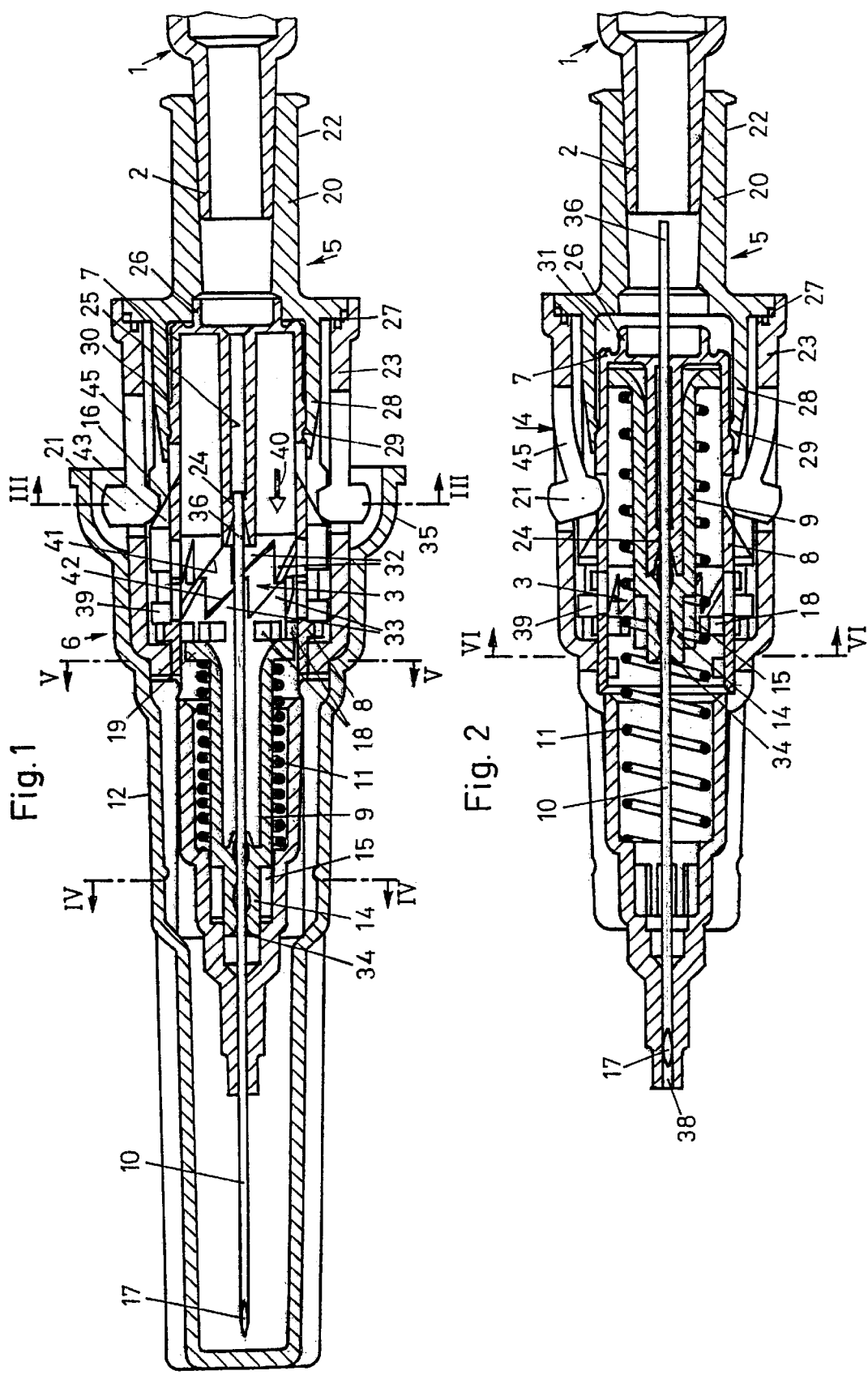

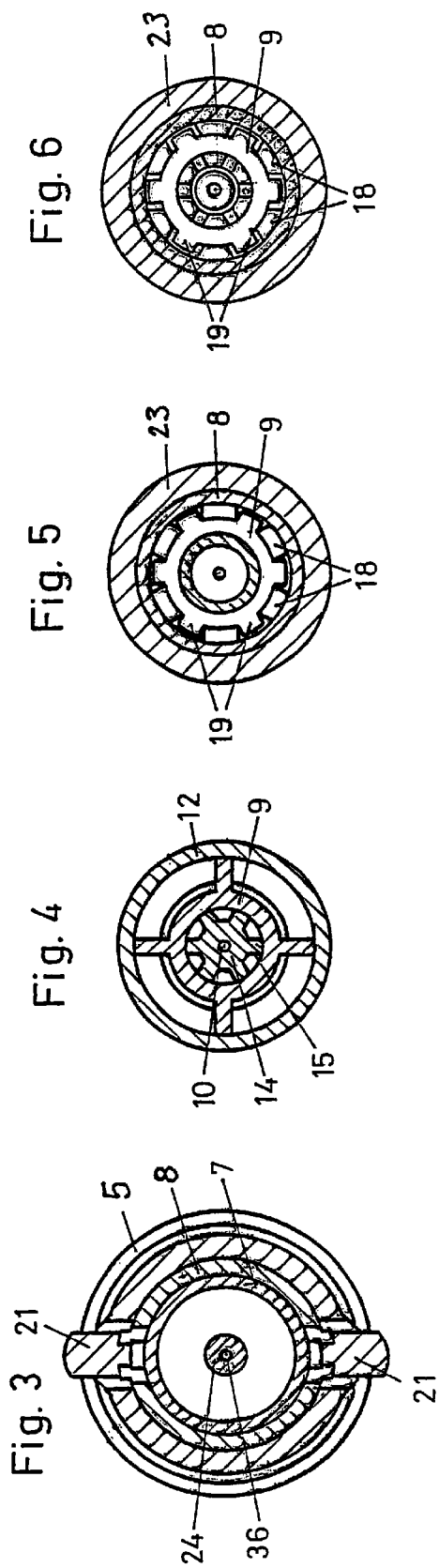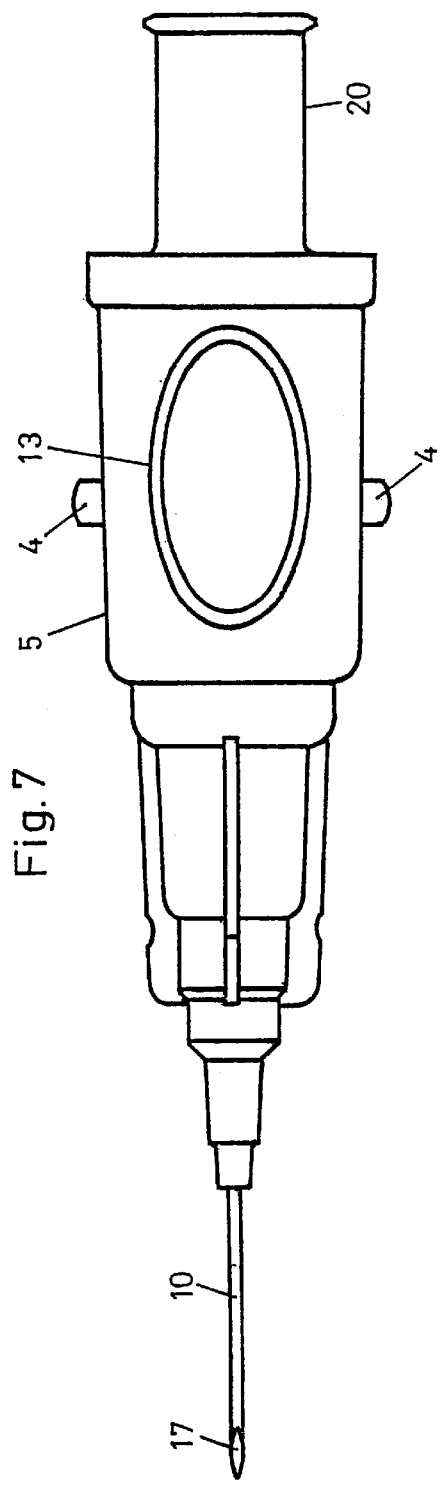

CANNULA FOR MEDICAL SYRINGES

BACKGROUND OF THE INVENTION

1. Field of the Invention

The invention relates to a syringe with a hollow needle and a needle holder attached to the hollow needle whereby the needle holder is retractable within the syringe housing and the needle may be retracted with the help of a device into the syringe housing after its use.

2. Description of the Related Art

A syringe of this type has been made known by the state-of-the-art of U.S. Pat. No. 5,480,385. This syringe has the problem that during retraction of the hollow needle, injection solution may be released through the needle and this injection solution might be mixed with the patient's blood.

A similar syringe has been made known by the state-of-the-art of U.S. Pat. No. 5,114,404. This syringe has the particular disadvantage in that the needle holder, together with the hollow needle, is turned during its release. Parts of tissue may be set free within the patient's body by turning of the needle, which represents a considerable risk of injury. Furthermore, another syringe was made known by EP-A-0 290 176, which also makes retraction of the needle possible after use. However, this syringe has a problem in that the needle may be in an arbitrary position in relation to its longitudinal orientation. The position of the needle point in relation to the syringe housing is hereby arbitrary and must first be determined before each injection. Retraction of the needle is caused here by means of a pressure spring and there is also the danger that the needle rotates during retraction. Other similar syringes have been made known by WO 92/16 248 and WO 92/058 18.

BRIEF SUMMARY OF THE INVENTION

The above-mentioned disadvantages and problems are avoided by the use of the innovative syringe in that the needle is secured against rotation within the syringe housing in a predetermined position and whereby retraction of the needle in this position is conducted without turning the needle in at least in a portion of the needle path. The portion of the needle path during which the needle remains non-rotating is preferably the foremost portion of the retraction path. The stabilization against needle rotation within the syringe housing makes it possible, for example, to mount the needle always in a predetermined position in relation to a marking on the syringe housing. Since the position of the needle point may be easily seen in the syringe housing, inspection of the needle point is not necessary and injection is thereby made easier and is also safer.

According to the invention, means for volume compensation during retraction of the needle are located in the syringe housing of a typical syringe. These means are designed, for example, in such a manner that a partial vacuum is created before retraction. The fluid displaced during needle retraction then compensates for this low pressure. Thereby it can be prevented that during needle retraction, injection solution is released through the needle, which might be mixed with the patient's blood.

According to a preferred development of the invention, the means for volume compensation show a movable element placed within the syringe housing, which may be moved before needle retraction to create a partial vacuum. According to further development of the invention, this movable element is at the same time a trigger element by which retraction is caused. This makes a design possible that has very few separate components.

According to further development of the invention, the hollow needle may be moved longitudinally at the circumference and the rear section where it has a seal. Thereby the danger of air injection is prevented by a high degree. At the same time, problems may be avoided during drawing of the injection solution into the syringe and settling of air bubbles is prevented. Since only a seal around the circumference of the needle has to be created, the to-be-sealed area is relatively small and causes a relatively small amount of friction during needle retraction. Additionally, the guiding parts stabilize the needle. According to one version, the syringe is equipped with a Luer nozzle that makes the use of the syringe possible in conjunction with standard hypodermic needles. However, the syringe may also be attached rigidly to a barrel.

According to further development, triggering the retraction is possible at any time whenever the needle retraction is caused by actuating elements, which are located inside the syringe in a radial manner and which move against one another. These actuating elements are preferably attached to the syringe housing. Steady handling of the syringe is achieved by the counter movement of the actuating elements and thereby unnecessary movement of the syringe is avoided.

Additional advantageous characteristics are shown in the related patent claims and the following specifications and drawings.

BRIEF DESCRIPTION OF THE DRAWINGS

One version of the invention is subsequently described in more detail by drawings. The following is shown:

FIG. 1 A longitudinal view of an innovative syringe in its basic position and a longitudinal view of a portion of a syringe barrel.

FIG. 2 A longitudinal view relating to FIG. 1, without a protective cap illustrating a retracted needle.

FIG. 3 A cross-sectional view along line Ill—Ill of FIG. 1.

FIG. 4 A cross-sectional view along line IV—IV of FIG. 1.

FIG. 5 A cross-sectional view along line V—V of FIG. 1.

FIG. 6 A cross-sectional view along line VI—VI of FIG. 2.

FIG. 7 A view of the innovative syringe without a protective cap.

DETAILED DESCRIPTION OF THE INVENTION

The illustrated syringe 6 shown in FIG. 1 in its basic position is detachable and is connected to an only partially shown barrel 1. The connection between the syringe 6 and the barrel 1 consists of a fitting 20 at the rear portion of the syringe housing 5 and a conical fitting 2 at the front portion of the barrel 1. The connection surface between fitting 2 and 20 is conical and corresponding to the known Luer connections. Such connections are well known in medical syringes. The housing 5 may also be connected rigidly with the barrel 1 according to a version not illustrated here.

The syringe housing 5 consists of a rear housing section 22 and a front housing section 23, which are joined together at a connection point 27 by ultrasonic welding. A detachable protective cap 12 is placed on the front portion of the housing 5, which prevents touching of the needle and which also covers with its rear bell-shaped rim 35 two actuating elements 4 that retract the needle 10.

The hollow needle 10 has the usual sharp point 17 and is firmly connected to the needle holder 9 at its middle portion by means of an adhesive section 34. The needle holder 9 has at its rear section several outwardly pointing teeth 19, which are resting correspondingly against inwardly pointing teeth 18 of a switching box 8. The force of a pressure spring 11 applies tension on the needle holder 9 and against the above-mentioned teeth 18. The needle 10 protrudes with its rear portion 36 into a longitudinal channel 25 of element 7 and is sealed at its outer movable side with an encircling sealing lip 24. Element 7 functions as a trigger element as well as a volume-compensating device as described in more detail later on. Element 7 is guided by a shell-shaped fitting 28 at the rear housing section 22 and is sealed by an encircling sealing lip 29 and is also held in place in the shown position by an interlocking beaded rim 26.

The needle holder 9 has at its front area 14 a ratchet-like cross section as shown in FIG. 4, and is guided by a corresponding guiding channel 15 in the syringe housing 5 to prevent turning. The needle holder 9 is placed into the guiding channel 15 in such a manner that the angular ground point 17 always remains in the same position in relation to the above-mentioned marking 13 in FIG. 7. The position of the point 17 may thereby be seen by the marking 13 on the syringe housing.

The needle 10 and the needle holder 9 may be fully retracted into the syringe housing 5 after use of the syringe 6. Retraction is caused by the release of tension of the pressure spring 11. To trigger the retraction, the switching box 8 is rotated until the teeth 18 are located in an opening between the teeth 19 as shown in FIG. 6. The needle holder 9 is thereby no longer blocked at the switching box 8 and is then moved to the rear by the pressure spring 11 into the position shown in FIG. 2. The point 17 is hereby placed safely into a channel 38 of the housing 5. It is essential that the retraction of the needle 10 is guided and turning is prevented at least during the first phase of retraction. The switching box 8 is turned when triggering the retraction, however, the needle holder 9 is not turned. The needle holder 9 is also kept from turning during retraction and during engagement into the guiding channel 15. In addition, the needle 10 is supported during retraction within the channel 38 and is also supported by the sealing lip 24.

The switching box 8 is a part of the switching mechanism 3 and rests movably against the projection 39 in the syringe housing 5. To be able to turn, the switching box 8 has switching teeth 33 at its back side that engage into corresponding switching teeth 32 of element 7. To actually turn the switching box 8, element 7 is moved in the direction of the arrow 40 whereby the slanted engagement surface 41 of the teeth 32 come into contact with the angled engagement surface 42 of the teeth 33. Turning of the element 7 is thereby prevented by wedge-shaped blocks 43 that protrude in a circle toward the outside. Element 7 is moved with an actuating device that has two opposing actuating elements 4. These actuating elements 4 have each an actuating cam 21 that is elastically molded to an arm 45 in the forward housing section 23. The actuating cam 21 is moved radial toward the inside to cause retraction triggering of the needle 10 and thereby a force is transferred onto the slanted engagement surface 16, which in turn causes movement of element 7 in the direction of the arrow 40. The protective cap 12 is naturally removed when operating the actuating element. Triggering of the retraction is not possible while the protective cap 12 is in place since the cams 21 can not be reached. When moving the element 7 in the direction of the arrow 40, a volume compensating space 31 is created that causes low pressure inside the syringe housing 5. Thereby it is prevented that existing fluid is pushed out of the needle point 17 during retraction of the needle 10. Element 7 serves thereby as a trigger element and as a volume compensating mechanism. At the same time, element 7 serves to seal the needle 10 at its rear section 36 and also serves as a guide.

Functioning of the syringe 6 will be subsequently described in more detail.

The protective cap 12 is removed from the syringe housing 5 to fill the barrel 1 with fluid, specifically with medicine. The point 17 of the needle 10 is submerged into the prepared fluid and the not-illustrated common plunger of the barrel is actuated correspondingly, whereby the fluid flows through the needle 10 and through the sealed channel 25 within the barrel 1. As commonly done during administration of an injection, air may be pushed out before an injection is given by briefly lifting the plunger. Thereby it is prevented that air bubbles are created and are eventually set free by a position change and are then injected. When the barrel 1 is filled with fluid, then the needle 10 is inserted in the usual manner whereby the marking 13 shows the position of the needle point 17. The marking 13 shows in an aseptic manner the slanted part of the needle point 17. The fluid is then injected in a common manner by lifting the plunger cylinder. After injection, the above-mentioned retraction of the needle 10 is hand triggered by firmly pressing the actuating element 4. The needle 10 is thereby guided and moved into the position shown in FIG. 2, whereby an unintentional touching of the needle 10 is no longer possible.

The syringe 6 is shown here in conjunction with a barrel 1. However, conceivable is also the use of the syringe 6 for withdrawal of blood, for example, or for in-vitro diagnostics. The removal of the syringe 6 may not be necessary during uses of such kind. All components, except for the needle 10 and the spring 11, may be manufactured as plastic injection molded parts. The number of these parts is comparatively small and assembly is suited also for series production. The relatively small volume requirements are also of importance, so that there is essentially little difference between the innovative syringe 6 and the common syringe without needle retraction.

What is claimed is:

1. A syringe comprising: a hollow needle (10), a needle holder (9) attached to the needle (10), a syringe housing (5) adapted to receive the needle holder (9) upon retraction of the needle holder (9), and a device (3) that has a switching mechanism (7,8) by which the hollow needle (10) may be retracted into the syringe housing (5); wherein the syringe includes a guiding channel (15), and the needle holder (9) is placed in the guiding channel, the guiding channel preventing the needle (10) from turning in the syringe housing (5) and maintaining the needle (10) in a predetermined position during retraction of the needle; and wherein the syringe further comprises two opposing actuating elements that are adapted to be manually moved in a direction inwardly of the syringe, the two opposing actuating elements operable to trigger the switching mechanism to retract the hollow needle.

2. A syringe according to claim 1, characterized in that the syringe housing (5) has on its exterior side a marking (13), which shows the position of the needle (10).

3. A syringe according to claim 1, characterized in that the needle holder (9) further includes a portion to prevent turning (14), the portion having a non-circular cross section, and wherein the guiding channel also has a non-circular cross section for cooperation with the portion of the needle holder.

4. A syringe according to claim 1, wherein said switching mechanism further comprises a movable compensating part that creates, upon retraction of the needle, a volume compensation space within the syringe housing having low pressure so as to prevent fluid within the needle from accidentally existing at a needle point.

5. A syringe according to claim 4, characterized in that the switching element (7) is a shell-shaped device that is moved within the syringe housing (5) during triggering of retraction of the needle.

6. A syringe according claim 1, characterized in that the needle (10) has a seal around its circumference and maintains said seal when moved longitudinally.

7. A syringe according to claim 4, characterized in that the needle (10) is sealed off from the movable compensating part located within the syringe housing (5).

8. A syringe according to claim 1, wherein the actuating elements (4) move radially toward an inside of the syringe in opposing directions.

9. A syringe according to claim 8, characterized in that the actuating elements (4) are molded to the syringe housing (5).

10. A syringe according to claim 8, characterized in that the actuating elements (4) move a trigger portion of the switching mechanism during operation, and wherein the trigger portion is located in the syringe housing (5).

11. A syringe according to claim 10, characterized in that the trigger portion is moved forward in the direction of the needle (10).

12. A syringe according to claim 10, characterized in that the trigger portion operates in conjunction with a switching box (8) that is located inside the syringe housing (5) and that the needle holder (9) is supported by said switching box (8).

13. A syringe according to claim 12, characterized in that the switching box (8) is mounted in a manner where it may be rotated.

14. A syringe according to claim 12, wherein the needle holder (9) further comprises projections (19) facing outwardly, and the switching box (8) has projections (18) facing inwardly, and wherein said projections (18) of the switching box are adapted to rest against the projections of the needle holder.

15. A syringe according to claim 1, characterized in that a detachable protective cap (12) is placed on the syringe housing (5), and whereby said protective cap (12) covers part of the actuating elements that trigger retraction of the needle (10).

16. A syringe according to claim 1, characterized in that the syringe housing (5) has a Luer nozzle (20).

17. A syringe according to claim 1, characterized in that the syringe is rigidly attached to a barrel (1).

18. A syringe comprising:
a hollow needle,
a needle holder attached to the hollow needle,
a syringe housing adapted to house the needle holder,
a switching mechanism operable to retract the hollow needle into the syringe housing, and
two opposing actuating elements disposed at the syringe housing so as to be manually moved in a direction radially inward of the syringe, the two opposing actuating elements operable to trigger the switching mechanism to retract the hollow needle.

19. The syringe according to claim 18, wherein, each of said two opposing elements includes a flexible arm member secured at one end of the arm to the syringe and an actuating cam at the other end of the arm, and wherein said actuating cam is adapted to engage a corresponding follower of the switching mechanism, said corresponding follower is disposed on an outside of said switching mechanism in a radial direction of said syringe and adapted to axially move said switching mechanism in response to an inward movement of said corresponding opposing element so as to retract the needle.

20. A syringe comprising:
a hollow needle,
a needle holder attached to the hollow needle,
a syringe housing adapted to house the needle holder,
a switching mechanism operable to retract the hollow needle into the syringe housing, and
two opposing actuating elements adapted to be manually moved in a direction inwardly of the syringe, the two opposing actuating elements operable to trigger the switching mechanism to retract the hollow needle; and
wherein, each of said two opposing elements includes a flexible arm member secured at one end of the arm to the syringe and an actuating cam at the other end of the arm, and wherein said actuating cam is adapted to engage a corresponding follower of the switching mechanism, said corresponding follower is disposed on an outside of said switching mechanism in a radial direction of said syringe and adapted to axially move said switching mechanism in response to an inward movement of said corresponding opposing element so as to retract the needle.

* * * * *